United States Patent [19]
Henderson et al.

[11] Patent Number: 5,703,191
[45] Date of Patent: Dec. 30, 1997

[54] METHOD FOR PURIFYING POLYALKYLSILOXANES AND THE RESULTING PRODUCTS

[75] Inventors: Danny L. Henderson, Wilmington, N.C.; Dale R. Powers, Painted Post, N.Y.

[73] Assignee: Corning Incorporated, Corning, N.Y.

[21] Appl. No.: 574,961

[22] Filed: Dec. 19, 1995

[51] Int. Cl.$^6$ .................................................. C08G 77/12
[52] U.S. Cl. ........................ 528/31; 528/10; 528/502 R; 556/460
[58] Field of Search ..................... 556/460; 528/10, 528/31, 502 R

[56] References Cited

U.S. PATENT DOCUMENTS

| | | |
|---|---|---|
| 2,239,551 | 4/1941 | Dalton et al. . |
| 2,269,059 | 1/1942 | McLachlan, Jr. . |
| 2,272,342 | 2/1942 | Hyde . |
| 2,326,059 | 8/1943 | Nordberg . |
| 3,117,838 | 1/1964 | Sterling et al. . |
| 3,416,890 | 12/1968 | Best et al. . |
| 3,486,913 | 12/1969 | Zirngibl et al. . |
| 3,666,414 | 5/1972 | Bayer . |
| 3,698,936 | 10/1972 | Moltzan . |
| 4,096,160 | 6/1978 | Ashby .................................. 556/460 |
| 4,156,689 | 5/1979 | Ashby et al. . |
| 4,242,487 | 12/1980 | Yajima et al. . |
| 4,491,604 | 1/1985 | Lesk et al. . |
| 4,501,602 | 2/1985 | Miller et al. . |
| 4,689,420 | 8/1987 | Baile et al. . |
| 4,810,673 | 3/1989 | Freeman . |
| 4,824,985 | 4/1989 | Goodwin et al. ..................... 556/460 |
| 5,043,002 | 8/1991 | Dobbins et al. . |
| 5,078,092 | 1/1992 | Antos et al. . |
| 5,125,946 | 6/1992 | Bhagavatula . |
| 5,152,819 | 10/1992 | Blackwell et al. . |
| 5,253,319 | 10/1993 | Bhagavatula . |
| 5,356,451 | 10/1994 | Cain et al. . |
| 5,473,037 | 12/1995 | Itoh et al. . |
| 5,516,870 | 5/1996 | Biggs et al. . |

FOREIGN PATENT DOCUMENTS

| | | |
|---|---|---|
| 60-90838 | 5/1985 | Japan . |
| 4-63019 | 6/1989 | Japan . |
| 6-166522 | 6/1994 | Japan . |
| 2 245 553 | 1/1992 | United Kingdom . |
| WO 94/10228 | 5/1994 | WIPO . |

OTHER PUBLICATIONS

"Information about Volatile Silicone Fluids", 1982 Dow Corning Corporation.
"Kinetics of the Thermolysis of Octamethylcyclotetrasiloxane in the Gas Phase" by Iain M. T. Davidson & John F. Thompson, Dept. of Chemistry, The University, Leicester LEI 7RH, pp. 2260–2265.
"Kinetics of the Oxidation of Octamethylcyclotetrasiloxane in the Gas Phase" by Iian M. T. Davidson & John F. Thompson, Dept. of Chemistry, The University, Leicester, LEI 7RH, pp. 1088–1095.
"Methylpolysiloxanes" by Winton Patnode & Donald F. Wilcock, Contribution from the Research Laboratory of the General Electric Co., vol. 68, pp. 358–363.
"The Mechanism of the Acid– and Base–catalyzed Equilibration of Siloxanes" by Simon W. Kantor, Willard T. Grubb and Robert C. Osthoff, Contribution from the General Electric Research Laboratory, vol. 76, pp. 5190–5197.
"The Acid–catalyzed Polymerisation of Cyclosiloxanes. Part I. The Kinetics of the Polymerisation of Octamethylcyclotetrasiloxane Catalyzed by Anhydrous Ferric Chloride– Hydrogen Chloride" by T. C. Kendrick, 1965, pp. 2027–2035.
"Sensitivity of the Siloxane Linkage Towards Acidolytic Cleavage" by Dr. K. Damm, Dr. D. Golitz, and Prof. Dr. W. Noll, Anorganische Abteilung der Farbenfabriken Bayer AG., Leverkusen (Germany), Angew. Chem. internat. Edit./ vol. 3 (1964)/No. 4, p. 310; with untranslated German article, Nov. 1965, pp. 1–14.
"Equilibria between Linear and Cyclic Polymers in Methylpolysiloxanes" by Donald W. Scott, Contribution from the Research Laboratory, General Electric Company, vol. 68, pp. 2294–2298.
"Organo–Silicon Polymers. The Cyclic Dimethyl Siloxanes," by M. J. Hunter, J. F. Hyde, E.L. Warrick and H.J. Fletcher, Contribution from Dow Corning Corporation, Midland, MI, Apr. 1946, vol. 68, pp. 667–672.
"Organosilicon Polymers. II. The Open Chain Dimethylsiloxanes with Trimethylsiloxy End Groups," by M.J. Hunter, E.L. Warrick, J.F. Hyde and C.C. Currie, Contribution from Dow Corning Corporation, vol. 68, pp. 2284–2290.

(List continued on next page.)

*Primary Examiner*—Melvyn I. Marquis
*Attorney, Agent, or Firm*—Edward F. Murphy

[57] ABSTRACT

The present invention is directed to a purified polyalkylsiloxane composition having a boiling point, under atmospheric conditions, of less than about 250° C. and containing high boiling impurities, including siloxanes and silanol-terminated siloxanes, that have boiling points, under atmospheric conditions, of greater than about 250° C. in a total concentration of less than 14 ppm. The present invention is further directed to a method of producing a purified polyalkylsiloxane composition, having a boiling point, under atmospheric conditions, of less than about 250° C., by distilling a polyalkylsiloxane starting material containing high boiling impurities having boiling points, under atmospheric conditions, of greater than about 250° C. in a total concentration of at least 14 ppm, under conditions effective to produce a purified polyalkylsiloxane composition having a boiling point under atmospheric conditions of less than about 250° C., and containing high boiling impurities, having boiling points, under atmospheric conditions, of greater than about 250° C., in a total concentration of less than 14 ppm. In preferred embodiments, low boiling components (including silanols and preferably also hexamethylcyclotrisiloxane) are reduced to less than about 100 ppm. The present invention is further directed to a method of producing fused silica glass by conversion of the purified polyalkylsiloxane composition.

33 Claims, 7 Drawing Sheets

OTHER PUBLICATIONS

"Vapor Pressures of Poly(dimethylsiloxane) Oligomers," by Ora L. Flaningam, Analytical lResearch Laboratory, Dow Corning Corp., Midland, MI 48640, J. Chem. Eng. Data 1986, pp. 266–272.

"Vapor Pressure–Viscosity Relations in Methylpolysiloxanes," by Donald F. Wilcock, Contribution from the Research Laboratory of the General Electric Co., Apr. 1946, vol. 68, pp. 691–696.

"Studies on Siloxanes. I. The Specific Volume and Viscosity in Relation to Temperature and Constitution," by Charles B. Hurd, Contribution from the Research Laboratory of the General Electric Co., vol. 68, pp. 364–370.

"Flow Characteristics of Linear, End–Blocked Dimethylpolysiloxane Fluids," by Gordon C. Johnson, Silicones Div., Union Carbide Corp., Tonawanda, NY, J. Chem. Eng. Data, vol. 6, No. 2, pp. 275–278.

"Surface Tension of Octamethylcyclotetrasiloxane and Hexamethyldisiloxane and Their Solutions with Carbon Tetrachloride and n–Hexadecane," by Richard S. Myers and H. Lawrence Clever, Dept. of Chemistry, Emory University, Atlanta, GA 30322, J. Chem. Eng. Data, vol. 14, pp. 161–164.

"Mutual Diffusion in Octamethylcyclotetrasiloxane Mixtures," by K.N. Marsh, Dept. of Physical & Inorganic Chemistry, The University of New England, Armidale, N.S.W., Australia, pp. 894–901.

"Mutual Solubilities in Water–Permethylsiloxane Systems," by G.E. Vogel and F.O. Stark, The Dow Corning Corp., Midland, MI, J. Chem. Eng. Data, Oct. 1964, vol. 9, No. 4, pp. 599–604.

"The Analytical Chemistry of Silicones," edited by A. Lee Smith, Analytical Research Dept., Dow Corning Corp., Midland, MI, 1991, and in that: Atomic Spectroscopy, by Nelson W. Lytle, Dow Corning Corp., Midland, MI, pp. 471–483.

"Measurement of Trace Silanol in Siloxanes by IR Spectroscopy," by Elmer D. Lipp, Analytical Research Dept. C041C1, Dow Corning Corp., Midland, MI, Soc. of applied Spectroscopy, vol. 45, No. 3, 1991, pp. 477–483.

"Physical Properties of Organosilicon Compounds. III. Thermodynamic Properties of Octamethylcyclotetrasiloxane," by Robert C. Osthoff and W.T. Grubb, Contribution from the Research Laboratory, General Electric Co., vol. 76, pp. 399–401.

"Comprehensive Organometallic Chemistry, *The Synthesis, Reactions and Structures of Organometallic Compounds,*" vol. 2, Editor: Sir Geoffrey Wilkinson, FRS, Imperial College of Science and Technology, University of London, Deputy Editor: F. Gordon A. Stone, FRS, Executive Editor: Edward W. Abel, 9.1.15.4 Linear and Cyclic Siloxanes, p. 160.

"Heat Transfer: Estimating Liquid Heat Capacity", by C.F. Chueh and A.C. Swanson, Halcon International, Inc., New York, NY, *Chemical Engineering Progress*, Jul. 1973, vol. 69, No. 7, pp. 83–85.

"5.5 High Temperature Thermal Behavior," *Depolymerization, Degradation and Thermal Properties*, by Clarson and Semlyen, pp. 230–244.

Brochure: "GE Silicones, Fluids," 1993, General Electric Co., Waterford, N.Y., pp. 1–16.

Specification Sheets, "GE Silicones Certifications", by Ben F. Mastrianni, General Electric Co., Waterford, N.Y., Jun. 13, 1995, 4 pages.

Provisional Application No. 60/008,889, filed Dec. 19, 1995, by D. Hawtof et al.

METHOD FOR PURIFYING POLYALKYLSILOXANES AND THE RESULTING PRODUCTS

FIELD OF THE INVENTION

The present invention relates to a method for purifying polyalkylsiloxanes, to a method of producing fused silica glass from purified polyalkylsiloxanes, and to the resulting purified polyalkylsiloxanes and fused silica glass products made therefrom.

BACKGROUND OF THE INVENTION

Various processes are known in the art that involve the production of metal oxides from vaporous reactants. Such processes require a feedstock solution, a means of generating and transporting vapors of the feedstock solution (hereafter called vaporous reactants) and an oxidant to a reaction site, and a means of catalyzing oxidation and combustion coincidentally to produce finely divided, spherical aggregates, called soot. This soot can be collected in any number of ways, ranging from a collection chamber to a rotating mandrel. It may be simultaneously or subsequently heat treated to form a non-porous, transparent, high purity glass article. This process is usually carried out with specialized equipment having a unique arrangement of nozzles and burners.

Much of the initial research that led to the development of such processes focused on the production of bulk fused silica. Selection of the appropriate feedstock was an important aspect of this work. Consequently, it was, at that time, determined that a material which could generate vapor pressure of 200–300 Torr at temperatures below 100° C. would be useful for making such bulk fused silica. The high vapor pressure of silicon tetrachloride ($SiCl_4$) suggested its usefulness as a convenient vapor source for soot generation and launched the discovery and use of a series of similar chloride-based feedstocks. This factor, more than any other, is responsible for the presently accepted use of $SiCl_4$, $GeCl_4$, $POCl_3$, $ZrCl_4$, $TiCl_4$, and $BCl_3$ as vapor sources, even though these materials have certain chemically undesirable properties. Returning to $SiCl_4$, it has been the industry standard over the years for the production of high purity silica glasses. As disclosed in U.S. Pat. No. 3,698,936, one of several reactions may take place to produce high purity fused silica via oxidation of $SiCl_4$; namely:

(1) $SiCl_4 + O_2 \rightarrow SiO_2 + 2Cl_2$, (2) $SiCl_4 + \frac{2}{3}O_3 \rightarrow SiO_2 + 2Cl_2$, or (3) $SiCl_4 + 2H_2O \rightarrow SiO_2 + 4HCl$, whereby burners or jet assemblies are utilized in feeding the reactant gases and vapors to a reaction space. It should be noted that reaction (2) rarely occurs or is used. There are inherent economic disadvantages to each of these reactions. Moreover, these reactions, which oxidize $SiCl_4$ through pyrolysis and hydrolysis, have the disadvantage of producing noxious and corrosive hydrochloric acid or chlorine by-products.

While the first two reactions occur theoretically, an auxiliary fuel is generally needed to achieve pyrolytic temperature. As to the third reaction, the hydrolysis of $SiCl_4$ results in the formation of hydrochloric acid (HCl), a by-product that is detrimental not only to many deposition substrates and to reaction equipment but also is harmful to the environment. Emission abatement systems have proven to be very expensive due to down-time, loss, and maintenance of equipment caused by the corrosiveness of HCl. The handling and disposal problems of the HCl by-product notwithstanding, the third reaction, hydrolysis of $SiCl_4$, tends to be the preferred commercial method of producing fused silica for economic reasons.

Though hydrolysis of $SiCl_4$ has been the preference of industry for producing high purity fused silica over the years, the enhanced global sensitivity to environmental protection has led to more strict government regulation of point source emissions, prompting a search for less environmentally pernicious feedstocks. Point source emission regulations require that HCl, the by-product of hydrolyzing $SiCl_4$, be cleansed from exhaust gases prior to their release into the atmosphere. The economic consequences of meeting these regulations have made commercial production of fused silica from halide-based feedstocks less attractive to industry.

As an alternative, high purity fused quartz or silica has also been produced by thermal decomposition and oxidation of silanes. Silanes are silicon-containing compounds analogous to hydrocarbons in which silicon is substituted for carbon. (For clarity, we note that siloxanes are compounds having an oxygen atom bonded to two silicon atoms, viz. Si—O—Si.) However, thermal decomposition and oxidation requires taking safety measures in handling because of the violent reaction that results from the introduction of air into a closed container of silanes. Silanes react with carbon dioxide, nitrous oxide, oxygen, or water to produce high purity materials that are potentially useful in producing, among other things, semiconductor devices. However, silanes have proven to be much too expensive and reactive to be considered for commercial use except possibly for small scale, extremely high purity applications.

A number of patents describe the production of high purity metal oxides, particularly fused silica, from a chloride-based feedstock. These patents disclose equipment with a number of burner arrangements and feedstock delivery systems to achieve oxidation of a metal chloride through flame hydrolysis or pyrolysis. Illustrative of this is U.S. Pat. No. 4,491,604 to Lesk et al., where trichlorosilane, dichlorosilane, and silicon tetrachloride are flame hydrolyzed to form soot, and U.S. Pat. No. 3,666,414 to Bayer, where silicon halides such as trichlorosilane are flame hydrolyzed. In similar processes, U.S. Pat. Nos. 3,486,913 to Zirngibl ("Zirngibl") and 2,269,059 to McLachlan ("McLachlan") teach oxidation of halides. Volatilized inorganic halide components such as $TiCl_4$, $CrCl_3$, $CrO_2Cl_2$, $SiCl_4$, $AlCl_3$, $ZrCl_4$, $FeCl_2$, $FeCl_3$, $ZnCl_2$, or $SnCl_4$ that are oxidized with air, steam, or oxygen are employed in Zirngibl, while silicon halides, ethyl silicate, methyl borate, $TiCl_4$, $AlCl_3$, and $ZrCl_4$ are used by McLachlan.

U.S. Pat. No. 3,416,890 to Best et al. discloses a process for preparing finely-divided metal or metalloid oxides by the decomposition of a metal or metalloid perhalide in a flame produced by the combustion of an oxidizing gas and an auxiliary fuel, such as carbon disulfide, carbon selenide sulfide, thiophosgene, or other hydrogen-free compounds containing sulfur bonded directly to carbon.

U.S. Pat. No. 2,239,551 to Dalton discloses a method of making glass by decomposing a gaseous mixture of glass-forming compounds in a flame of combustible gas. The mixture is used in the formation of anhydrous oxides of silicon, aluminum, and boron. Decomposable compounds such as ethyl or methyl silicate, trichlorosilane, and silicon tetrafluoride may be substituted for silicon tetrachloride; methyl borate or boron hydride may be substituted for boron fluoride, etc.

U.S. Pat. No. 2,326,059 to Nordberg details a technique for making silica-rich ultra-low expansion glass by vaporizing tetrachlorides of Si and Ti into the gas stream of an oxy-gas burner, depositing the resultant mixture to make a preform, vitrifying the preform at 1500° C. to make an opal glass, and firing the opal preform at a higher temperature to cause it to become transparent.

U.S. Pat. No. 2,272,342 to Hyde discloses a method of producing glass articles containing vitreous silica by vaporizing a hydrolyzable compound of silicon such as silicon chloride, trichlorosilane, methyl silicate, ethyl silicate, silicon fluoride, or mixtures thereof, using a water bath. The silicon compound vapor is hydrolyzed by water vapor in the flame of a burner, and the resulting amorphous oxide is collected and subsequently sintered until a transparent glass results.

U.S. Pat. No. 4,501,602 to Miller et al. describes the production of particulate metal oxide soot utilizing β-diketonate complexes of metals from Groups IA, IB, IIA, IIB, IIIA, IIIB, IVA, IVB, and the rare earth series of the Periodic Table.

Also cited in the art are several patents where silane compounds have been used in producing high purity fused silica.

Japanese Patent Application No. 90838-1985 to Okamoto et al., discloses a method of doping quartz glass by utilizing an ester silane expressed by the general formula $R^1{}_nSi(OR^2)_{4-n}$ and one or more dopants defined by the formulas $Ge(OR^3)_3$, $B(OR^3)_3$, and $PH_3$, where $R^1$ is a hydrogen atom, methyl or ethyl group; $R^2$ is a methyl or ethyl group; $R^3$ is an univalent hydrocarbon group; and n is an integer ranging between 0 and 4. A great many organometallic compounds are disclosed, including methyltrimethoxysilane, dimethyldimethoxysilane, trimethylmethoxysilane, tetramethoxysilane, methyltriethoxysilane, and tetraethoxysilane.

U.S. Pat. No. 3,117,838 to Sterling describes a method of producing very pure fused quartz or silica by the combined thermal decomposition and oxidation of silanes, where either carbon dioxide, nitrous oxide, or water vapor and a silane are fed into a burner or torch jet and the flame is allowed to impinge on a carbon substrate upon which silica is deposited.

U.S. Pat. No. 4,810,673 to Freeman discloses a method of synthesizing high quality silicon oxides by chemical vapor deposition of a source gas mixture which includes a halogenated silane component and an oxygen source, namely, dichlorosilane and nitrous oxide.

U.S. Pat. No. 4,242,487 to Hasegawa et al. discloses a method of producing a heat resistant, semi-inorganic compound that is useful as a raw material for making various heat-resistant materials by reacting an organoborosiloxane compound with at least one of the group of aliphatic polyhydric alcohols, aromatic alcohols, phenols, and aromatic carboxylic acids at 250° C. to 450° C. in an inert atmosphere.

As is clear from the preceding discussion, it is highly desirable for both economic and environmental reasons to find halide-free silicon compounds to replace the silicon halide feedstocks typically used to produce high purity silica glass. Such halide-free starting materials would produce carbon dioxide and water, rather than noxious and corrosive $Cl_2$ and HCl, as by-products of the glass-making process.

U.S. Pat. No. 5,043,002 to Dobbins et al., the disclosure of which is hereby incorporated by reference, discloses the usefulness of polymethylsiloxanes, in particular, polymethylcyclosiloxanes such as hexamethylcyclotrisiloxane, octamethylcyclotetrasiloxane, and decamethylcyclopentasiloxane in a method of making fused silica glass. The method can be applied to the production of a non-porous body of silica glass doped with various oxide dopants and for the formation of optical waveguide fibers. U.S. Pat. No. 5,043,002 to Dobbins et al. also discloses the use of hexamethyldisiloxane; see also reference to hexamethyldisiloxane in Japanese Patent Application No. 1-138145.

U.S. Pat. No. 5,152,819 to Blackwell et al., the disclosure of which is hereby incorporated by reference, describes additional halide-free silicon compounds, in particular, organosilicon-nitrogen compounds having a basic Si—N—Si structure, siloxasilazones having a basic Si—N—Si—O—Si structure, and mixtures thereof, which may be used to produce high purity fused silica glass without the concomitant generation of corrosive, polluting by-products.

Although use of halide-free silicon compounds as feedstocks for fused silica glass production, as described in U.S. Pat. Nos. 5,043,002 and 5,152,819, avoids the formation of HCl, some problems remain, particularly when the glass is intended for the formation of optical waveguide fibers. Applicants have found that the presence of high boiling impurities in, for example, a polyalkylsiloxane feedstock, can result in the formation of gel deposits in the line carrying the vaporous reactants to the burner or within the burner itself. This leads to a reduction in the deposition rate of the soot preform that is subsequently consolidated to a blank from which an optical fiber is drawn. Furthermore, particulates of the high molecular weight, high boiling impurities may be deposited on the optical fiber blank, resulting in "defect" or "clustered defect" imperfections that adversely affect the quality of the subsequently drawn fiber and can require scrapping of an entire blank.

Defects are small (i.e. 0.1 to 4.0 mm in diameter) bubbles in a glass body. They can be formed in fused silica by an impurity, such as uncombusted gelled polyalkylsiloxane. A very small particle of siloxane gel can be the initiation site for a defect. The siloxane decomposes at high temperature after being deposited on the glass body, giving off gases which cause the formation of the defect.

Thermophoresis is the process by which soot is attracted to the preform. In fact, it produces the driving force which moves the particles towards the cooler preform. The hot gases from the burner pass around the preform during laydown; the soot particles do not have sufficient momentum by combustion alone to strike the preform. Thermophoresis moves particles in a temperature gradient from hot regions to cooler regions. The burnt gases from a burner are hotter than the preform. As these gases pass around the preform, a temperature gradient is produced. Hot gas molecules have higher velocity than cold gas molecules. When hot gas molecules strike a particle, they transmit more momentum to the particle than a cold gas molecule does. Thus, particles are driven towards the colder gas molecules and, in turn, toward the preform.

Clustered defects are larger glass defects found in optical fiber preforms. They are made up of a series of defects in the form of a line or a funnel- or flower-shaped cluster. A large particle of gel can be the initiation site for a clustered defect. After the gel particle has struck the porous preform, it causes a raised area to stand out from the preform surface. Because the clustered defect is a raised site, more heat transfer passes to this site. Because of this increased heat transfer, more thermophoresis occurs at this site, causing the imperfection to grow and leave behind a string of defects. As a result of the clustered defect, the affected portion of the optical fiber preform cannot be consolidated normally, and the consequent irregularity in the blank yields defective optical fiber.

Thus, there is a need for a purified polyalkylsiloxane composition having a very low concentration of high boiling impurities to serve as a feedstock for the production of high purity fused silica glass and articles formed therefrom, including optical waveguide fibers. The present invention is directed to fulfilling this need.

SUMMARY OF THE INVENTION

The present invention is directed to a purified polyalkylsiloxane composition having a boiling point, under atmospheric conditions, of less than about 250° C. and containing high boiling impurities, including siloxanes and silanol-terminated siloxanes, that have boiling points, under atmospheric conditions, of greater than about 250° C., in a total concentration of less than 14 parts per million ("ppm").

The present invention is further directed to a method of producing a purified polyalkylsiloxane composition, having a boiling point, under atmospheric conditions, of less than about 250° C., by distilling a polyalkylsiloxane starting material containing high boiling impurities having boiling points, under atmospheric conditions, of greater than about 250° C. in a total concentration of at least 14 ppm, under conditions effective to produce a purified polyalkylsiloxane composition having a boiling point, under atmospheric conditions, of less than about 250° C., and containing high boiling impurities that have boiling points, under atmospheric conditions, of greater than about 250° C., in a total concentration of less than 14 ppm.

According to preferred embodiments, relatively volatile, low boiling chemical species having a molecular weight less than or equal to that of hexamethyl cyclotrisiloxane (D3), including low molecular weight silanols and more preferably also D3 itself, are also removed.

The present invention is further directed to a method of producing fused silica glass by conversion to glass of the purified polyalkylsiloxane composition containing high boiling impurities, having boiling points, under atmospheric conditions, of greater than about 250° C., in a total concentration of less than 14 ppm.

DETAILED DESCRIPTION OF THE INVENTION

Figure 1:
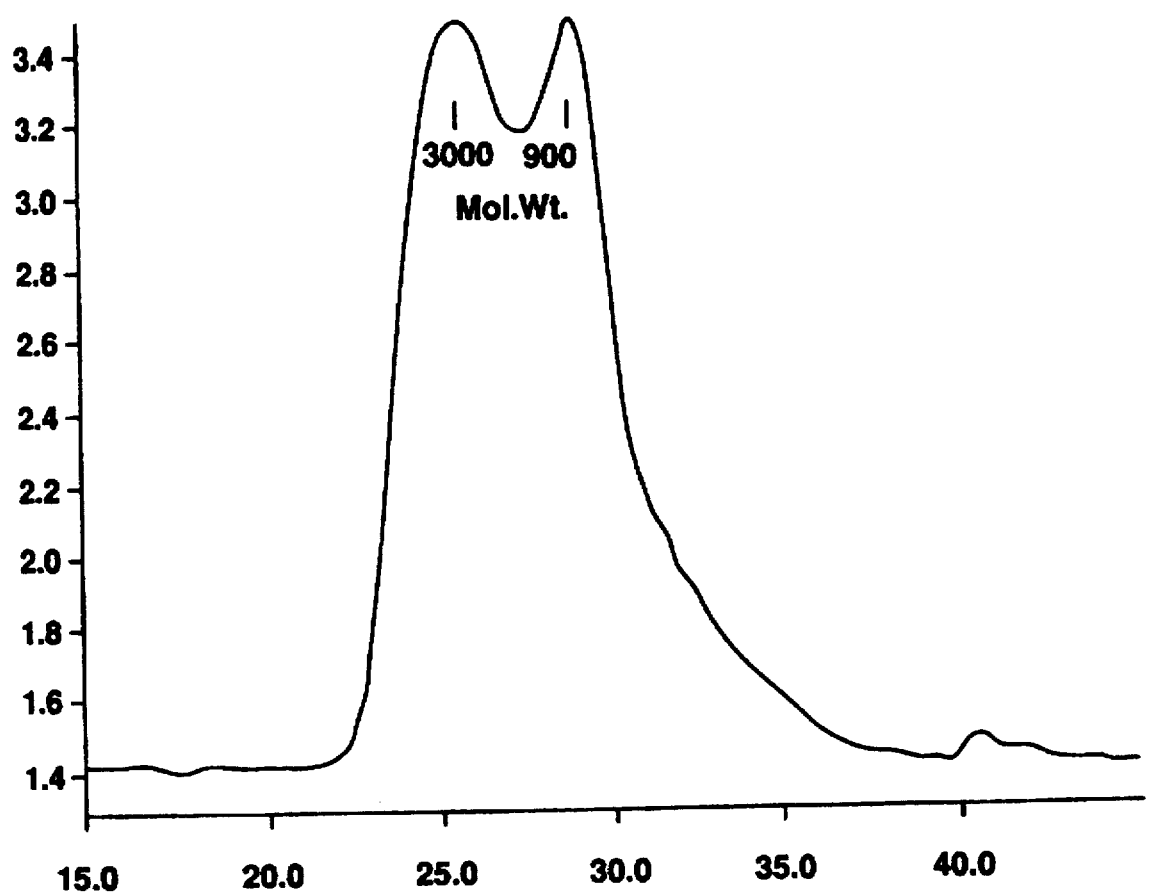
FIG. 1 is a gel permeation chromatographic trace showing the bimodal distribution of high molecular weight, high boiling impurities in a sample of octamethylcyclotetrasiloxane.
Figure 2:
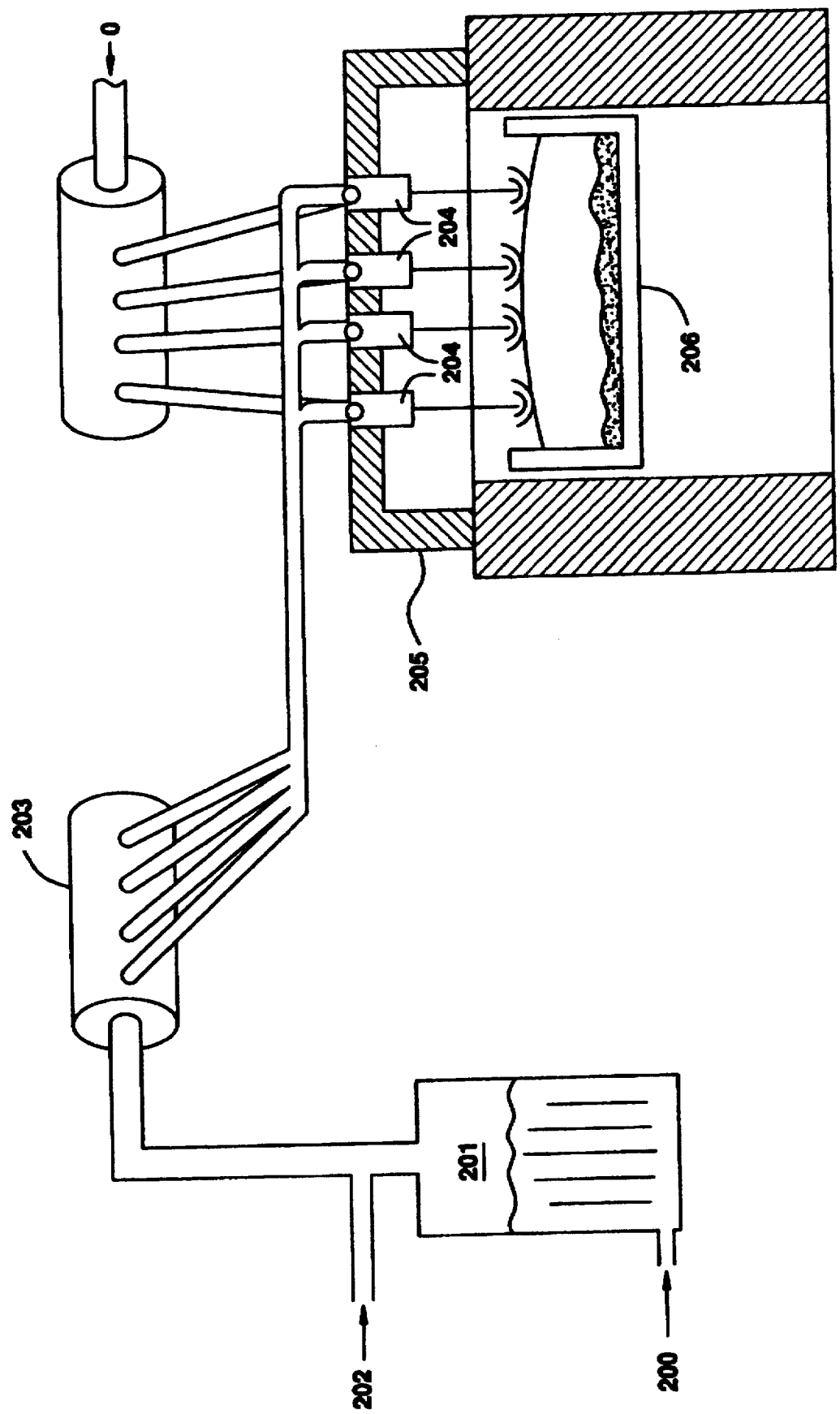
FIG. 2 is a schematic representation of an apparatus and process for forming large masses of fused silica.

Although polyalkylsiloxanes as feedstocks for the production of silica glass provide, as previously discussed, important advantages over the commonly employed $SiCl_4$, substantial practical difficulties have been encountered in their use. Commercially available siloxanes such as, for example, octamethylcyclotetrasiloxane contain high boiling impurities whose concentrations may range up to 200 ppm or more. The presence of these impurities in the siloxane feedstock result in deposits in the lines of the vapor delivery system, causing substantial lowering in the rate of soot deposition from the burner. This problem is aggravated when an oxidizing carrier gas such as oxygen is included in the reactant vapor stream, because oxidizers can catalyze polymerization of the siloxane feedstock. In addition, carry-over of the impurities into the soot can result in defects in the glass blanks. In the case of a typical 100 kilometer consolidated blank, which has a diameter of 70 millimeters (mm) and a length of 0.8 meter (m), the presence of one clustered defect on the surface of the blank will typically result in the loss of 5 kilometers of fiber on drawing. In the case of a larger consolidated blank, the negative impact of a single clustered defect is proportionately higher. In a 250 kilometer consolidated blank, which has a diameter of 90 mm and a length of 1.8 m, one clustered defect on the surface of the blank will typically result in the loss of 8 kilometers of fiber on drawing.

The presence of high boiling impurities in a polyalkylsiloxane feedstock for silica glass production will be problematic when the partial pressures of the impurities are greater than the vapor pressure of the polyalkylsiloxane being vaporized. Under these conditions, all of the impurities are not vaporized and tend to form gels on the vaporizer surfaces. On the other hand, when the partial pressures of the impurities are less than the vapor pressure of the polyalkylsiloxane being vaporized, fouling is not a problem, because vaporization conditions are sufficient to vaporize the feedstock totally.

In conventional polyalkylsiloxane synthesis processes, hydrolysis of an alkylhalosilane compound yields a mixture of polyalkylsiloxanes and silanols. The polyalkylsiloxane-silanol mixture is distilled to separate most of the silanols from the mixture. This can be achieved in a single distillation, or it can be accomplished with two or more sequential distillations. The resulting distillate is passed through a carbon filter and, then, a molecular sieve bed, thereby producing the polyalkylsiloxane starting material that is to be further purified through removal of high boiling impurities. Contacting silanes and siloxanes with charcoal and molecular sieves to remove platinum catalyst-poisoning impurities is described in U.S. Pat. No. 4,156,689 to Ashby et al., the disclosure of which is hereby incorporated by reference. While not wishing to be bound by theory, it is believed that the steps of carbon filtration and molecular sieve treatment in accordance with the present invention result, as a side effect, in the formation of at least a portion of the high boiling impurities in the polyalkylsiloxane starting material. These increased impurities are believed to result from condensation reactions involving lower boiling compounds, possibly including silanols, to produce high boiling linear or cyclic compounds. Such condensation reactions occur as follows:

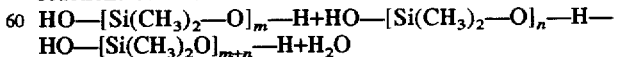

It is the presence of these impurities in concentrations of 14 ppm or more that causes the above-noted fouling and product quality problems. It is an objective of the present invention to reduce the concentration of such impurities to less than 14 ppm (and as low as 0.25 ppm or lower) by distillation.

In preferred embodiments, the polyalkylsiloxane is first passed through a carbon bed and then through a molecular sieve bed. As is known in the art, the carbon bed can catalyze polymerization of the silanols to yield high molecular weight compounds. The molecular sieve then traps these compounds because of their greatly increased molecular size.

In accordance with the present invention, a polyalkylsiloxane starting material containing high boiling impurities that have boiling points, under atmospheric conditions, of greater than about 250° C. is distilled to produce a purified polyalkylsiloxane composition having a boiling point, under atmospheric conditions, of less than about 250° C. The total concentration of high boiling impurities in the starting material is at least 14 ppm and can be up to about 200 ppm or even higher. The distillation, which is carried out at a temperature where the polyalkylsiloxane product vapor pressure exceeds the total pressure for the distillation, may be performed either at substantially atmospheric pressure or at reduced pressure under vacuum. This produces a purified polyalkylsiloxane composition having a total concentration of high boiling impurities of less than 14 ppm, more preferably less than about 6 ppm, still more preferably less than about 2 ppm, and most preferably less than about 0.25 ppm. The purified polyalkylsiloxane composition may have either a linear (e.g., hexamethyldisiloxane) or cyclic molecular structure but is preferably a polymethylcyclosiloxane selected from the group consisting of hexamethylcyclotrisiloxane (D3), octamethylcyclotetrasiloxane (D4), decamethylcyclopentasiloxane (D5), dodecamethylcyclohexasiloxane (D6), and mixtures thereof (The terms D3, D4, D5, D6, etc. are examples of the General Electric Co. siloxane notation, where D represents the group ($[(CH_3)_2Si]$—O—). Octamethylcyclotetrasiloxane (D4) is particularly preferred for use according to the present invention. Dodecamethylcyclohexasiloxane (D6) is usable, but it is least preferred, among the named cyclic species. The preparation of polymethylcyclosiloxanes is described in U.S. Pat. No. 4,689,420 to Baile et al., the disclosure of which is hereby incorporated by reference. Also encompassed by the polyalkylsiloxanes of the present invention are polymethylhydrocyclosiloxanes having hydrogen groups as well as methyl groups attached to the silicon atoms. For example, half of the methyl groups in octamethylcyclotetrasiloxane can be replaced with hydrogen groups to form tetramethylcyclotetrasiloxane. Additionally, ethyl groups can be substituted for all or some of the methyl or hydrogen groups.

When the purified polyalkylsiloxane composition is predominantly octamethylcyclotetrasiloxane, the distillation is preferably carried out under conditions where the vapor pressure of the octamethylcyclotetrasiloxane, in Torr, exceeds $\exp(15.56055-3128.52/(T-98.093))$, and, in Pascals, exceeds $\exp(20.4534-3128.52/(T-98.093))$, where T is the distillation temperature in degrees Kelvin. The separated high boiling impurities typically include a bimodal distribution of components whose median molecular weights are greater than about 900 grams/mole. This distribution in a typical sample of octamethylcyclotetrasiloxane is shown in FIG. 1, which plots the relative peak height of the concentration of species having a given molecular weight as the polyalkylsiloxane sample passes through the chromatography column versus time in minutes. Species of relatively high molecular weight pass through the gel quickly. Species of relatively low molecular weight pass through the gel more slowly.

The concentration of high boiling impurities in a polyalkylsiloxane material can be determined by two alternative procedures.

In the first (and preferred) procedure, a weighed amount of the polyalkylsiloxane material is placed in a round-bottomed flask attached to a rotary evaporator. The flask is placed in a heated water or oil bath, and the material is concentrated under vacuum to a small amount of oily residue. This residue is transferred to a smaller flask using a small volume of toluene, and the toluene-diluted material is again concentrated to an oil. After a second toluene-assisted transfer to a small tared vessel followed by re-concentration, the oily residue is weighed, thereby enabling the concentration of high boiling impurities in the polyalkylsiloxane material to be determined. An aliquot of this residue dissolved in toluene is subjected to gel permeation chromatographic analysis to determine the molecular weight distribution of the high boiling impurities.

The second alternative procedure for determining the concentration of high boiling impurities in a polyalkylsiloxane material, utilizes an evaporative light-scattering detector (ELSD). Commercially available equipment for this method includes an Alltech Varex MKIII detector, Alltech 426 HPLC Pump, and an Alltech 570 Autosampler. A sample of the polyalkylsiloxane material is nebulized in a pressurized gas such as nitrogen, and the nebulized material is passed through the detector, which is connected to the pump. The drift tube of the light-scattering detector, which is provided with a laser light source, is maintained at about 65°–85° C., preferably about 75° C. The laser light scattered by the particulates in the nebulized sample is detected, and an analog signal proportional to the light intensity is generated and detected. The detector response is a peak that can be displayed with either a chart recorder or a chromatographic integrator. Either peak height or area may be used for quantification of the response; area integration is preferred. The ELSD method is rapid and convenient but does not provide information as to the molecular weight distribution of the impurity components.

As noted above, the high boiling impurities can be in the form of siloxanes or silanol-terminated siloxanes. These siloxane impurities can include cyclic polyalkylsiloxanes having boiling points, under atmospheric conditions, of greater than 250° C. Dodecamethylcyclohexasiloxane (D6) has a boiling point lower than 250° C. and, therefore, does not constitute such an impurity, while tetradecamethylcycloheptasiloxane (D7), whose boiling point is higher than 250° C., is such an impurity.

In the presence of water, a cyclic polyalkylsiloxane may undergo a ring-opening reaction to form a linear silanol-terminated siloxane, as shown in the following general equation:

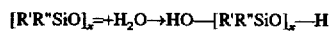

where R' and R" are alkyl groups.

The linear disilanol-siloxane compounds produced by hydrolytic ring-opening of preferred polymethylcyclosiloxanes such as D4 or D5 (χ equals 4 or 5, respectively, in the above equation) would, of course, have substantially reduced volatility compared with the latter compounds and might, therefore, be expected to result in deleterious gel deposits in the vapor reactant lines or the burner of the silica glass production equipment. Furthermore, the disilanol compounds produced in the above-described hydrolysis reaction are themselves highly reactive intermediates that readily undergo condensation reactions with their cyclosiloxane precursors, resulting in the formation of high boiling condensation products, as shown in the following general equation:

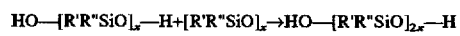

Such high boiling, low volatility materials, which may be either cyclic or non-cyclic in structure, are extremely likely to produce gel deposits in the production equipment. Hence, in accordance with the invention, it is necessary to provide polyalkylsiloxane feedstocks containing very low concentrations of these high boiling impurities to ensure efficient soot production.

Low boiling compounds remaining in the polyalkylsiloxane composition can include hexamethylcyclotrisiloxane (D3), and low molecular weight silanols, all having a molecular weight of 250 grams/mole or less. The silanol materials form $SiO_2$ and polyalkylsiloxane gel deposits very quickly in the polyalkylsiloxane fume tubes and burners. The D3 has a greater tendency than do D4, D5 or D6 to decompose, forming among other things $SiO_2$ which can then deposit in the fume tubes and burners. In cases where the burners being used are localized and do not traverse the entire length of the target for soot deposition, the soot deposits are non-uniform, which leads to non-uniform products. In preferred embodiments, these low molecular weight silanols are removed as an integral part of the distillation according to the invention. More preferably, the D3 is also removed, although we believe that the silanols present a comparatively greater problem. These relatively volatile materials will be vaporized at the beginning of the distillation process and then discarded. Preferably, the concentration of D3 and low molecular weight silanols is reduced to less than about 7000 ppm. More preferably, the concentration is reduced to less than about 100 ppm. Current technology does not facilitate separate measurement of D3 and low molecular weight silanol concentrations.

Further, in accordance with the present invention, a method of producing fused silica glass is provided. A purified polyalkylsiloxane composition having a boiling point, under atmospheric conditions, of less than about 250° C. and containing high boiling impurities having a boiling point, under atmospheric conditions, of greater than about 250° C. in a total concentration of less than 14 ppm, preferably less than about 6 ppm, still more preferably less than about 2 ppm, and most preferably less than about 0.25 ppm, is provided and converted to fused silica. The purified polyalkylsiloxane composition required to produce fused silica glass is obtained as described above.

The purified polyalkylsiloxane composition may be doped by mixing with a compound capable of being converted by oxidation or flame hydrolysis to $P_2O_5$ and/or a metal oxide with a metallic component selected from the group consisting of Group IA, IB, IIA, IIB, IIIA, IIIB, IVA, IVB, VA, rare earth series, and mixtures thereof. Preferred oxide dopants include $Al_2O_3$, $B_2O_3$, $GeO_2$, $P_2O_5$, and $TiO_2$.

In preferred embodiments, the purified polyalkylsiloxane is further stabilized against degradation prior to end-use, by sparging with an inert gas, e.g., nitrogen, in order to remove dissolved oxygen and water. Oxygen and water may, of course, react with and degrade the polyalkylsiloxane, which not only leads to the presence of undesired low molecular weight species in the composition, but may give rise to reactive species which might polymerize and lead to gel formation.

The purified polyalkylsiloxane composition is generally converted to fused silica glass by providing a gas stream containing entrained purified polyalkylsiloxane composition. We note, in passing, that alternatively the polyalkylsiloxane composition can be supplied in liquid form to a burner flame, as disclosed in a U.S. Provisional Patent Application 60/008889 filed on even date herewith in the names of Daniel W. Hawtof, Greg E. Smith and Eric H. Urruti entitled "Method and Apparatus for Forming Fused Silica By Combustion of Liquid Reactants", the contents of which are hereby incorporated by reference. Returning to our discussion, the gas stream is then oxidized to convert the polyalkylsiloxane composition to finely divided amorphous soot, which is deposited to produce a porous mass. The gas stream is provided by nebulizing or vaporizing the purified polyalkylsiloxane composition in a carrier gas such as an oxidizing gas, a combustible gas, an inert gas, or mixtures thereof. Particularly suitable gases are hydrogen, nitrogen, oxygen, or mixtures thereof. Where the selected carrier gas is not inert, and especially if it is an oxidizer such as oxygen, the carrier gas should be combined with the polyalkylsiloxane composition immediately before combustion.

The gas stream is oxidized by passing the gas stream through a combustion burner flame in the presence of oxygen. The soot may be deposited on or in a stationary bait or other known conventional target. Preferably, the soot is deposited on a rotating mandrel. The resulting porous mass may then be converted to a consolidated mass of fused silica glass by heating in a furnace preferably containing helium and chlorine. Also in accordance with the invention, the fused silica glass product may be further treated by, for example, drawing it into an optical fiber product.

The conventional boule process used in making bulk fused silica is a one-step process, while the conventional vapor deposition process used in making silica glass for optical waveguide applications is a three-step process.

In the conventional boule process, a carrier gas is bubbled through a feedstock that is maintained at a specified temperature. The vaporous reactant is entrained in the carrier gas and is thereby transported to the reaction site. The reaction site is comprised of a number of burners that combust and oxidize the vaporous reactant, typically at a temperature greater than 1700° C.

The aforementioned system is illustrated in FIG..2, where feedstock 201 comprises the purified polyalkylsiloxane composition of the invention that is to be combusted in a commercial furnace to produce boules of high purity fused silica. An inert gas, a combustible gas, an oxidizing gas, or mixtures thereof is used as carrier gas 200, and bypass stream 202 of a gas chosen from the same group is introduced to prevent saturation of the vaporous stream. The reactant is vaporized by the action of carrier gas 200 bubbled through feedstock 201, using apparatus such as that described in the above-mentioned references. Reactant is then passed through a distribution mechanism 203 to a reaction site having a number of burners 204 present in close proximity to a furnace crown 205. The reactant is combined with a fuel/oxygen mixture O at these burners and combusted and oxidized at a temperature greater than 1700° C. High purity metal oxide soot is directed downward through the refractory furnace crown 205, where it is immediately deposited and consolidated to a non-porous mass on a bait 206. It is well recognized in the art that processing of the feedstock requires an apparatus and transfer system capable of vaporizing the feedstock and delivering it to the burner in the vapor state.

Most of the processes being developed by industry today for the manufacture of optical waveguides employ the chemical vapor deposition (CVD) concept or a modified version thereof. The precursor vapors are entrained in a carrier gas stream and then passed through a burner flame, usually a natural gas/oxygen mixture and frequently containing excess oxygen. The vapors in the mixture are converted to their respective oxides upon exiting the burner orifice to form a stream of volatile gases and finely-divided, amorphous, spherical aggregates, called soot. The soot is collected on a mandrel or on or in a bait, where it is deposited in thin layers. The final product of soot collection, the porous preform, is then subjected to high temperature in which the preform consolidates to a non-porous monolithic glassy body. The steps of oxidation, soot deposition, and consolidation can be carried out either sequentially or simultaneously, as taught in U.S. Pat. No. 5,043,002 to Dobbins et al. and U.S. Pat. No. 5,152,819 to Blackwell et al., the disclosures of which are hereby incorporated by reference.

In usual practice, the optical waveguide process is a three-step process.

The first stage involves oxidizing reactant feedstock(s) to form finely-divided, amorphous spherical particles of soot on a substrate. In the second stage of the process, the blank or preform is subsequently heat treated in a helium/chlorine atmosphere to full consolidation. In the third and final stage, conventional fiber-draw technology is utilized in extracting optical waveguide fiber from the preform.

The first stage of this process can be carried out in a number of different ways.

In a first embodiment of the first stage, reactant is supplied in liquid form to a flow distributor that delivers the liquid to one end of a vaporization device. The liquid flows down a heated, inclined surface as a thin film toward a second end of the device. When the second end is reached, liquid has been converted to a vapor and is delivered to a burner for oxidation to soot particles. This embodiment is described in U.S. Pat. No. 5,356,451 to Cain et al., which is hereby incorporated by reference, and is shown in FIG. 3.

Figure 3:
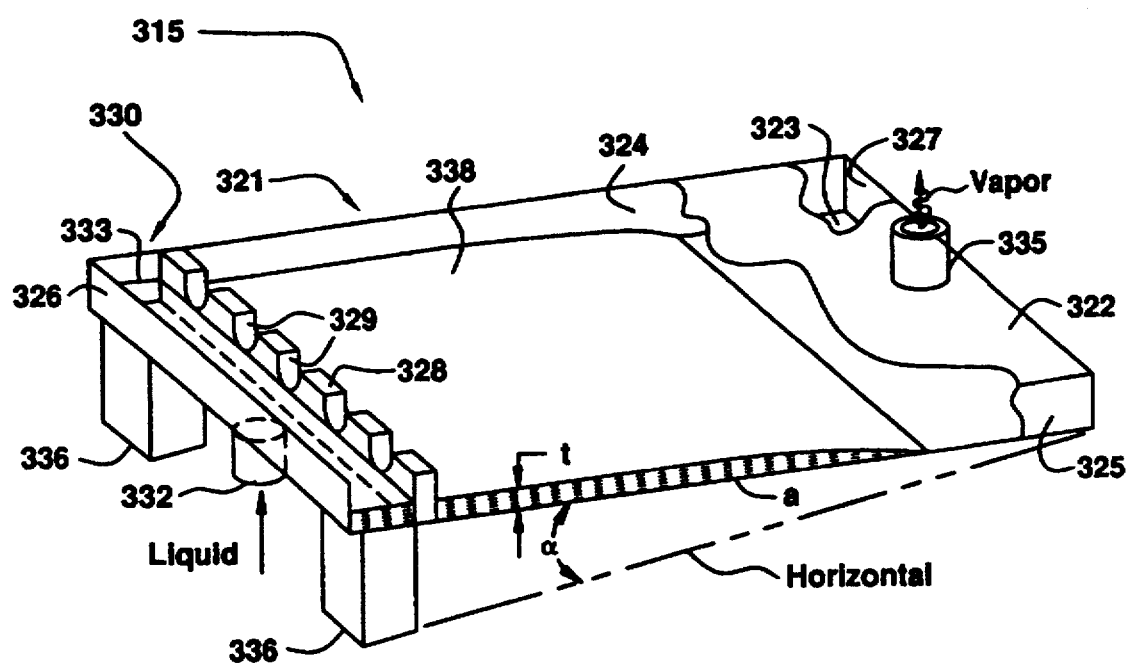
FIG. 3 is a perspective view of a first vaporizer embodiment useful in the production of optical waveguides.

Referring to FIG. 3, vaporizer 315 comprises a vaporization chamber 321 enclosed by top wall 322, bottom wall 323, side walls 324 and 325 and end walls 326 and 327. A flow distributor 328 having a plurality of U-shaped channels 329 is located near end wall 326, the space between flow distributor 328 and the end wall 326 constituting a liquid reservoir 330. Liquid input orifice 332 is situated at the bottom of reservoir 330, and vapor output orifice 335 is situated in top wall 322 near end wall 327.

Reactant liquid is fed into orifice 332. When the level of the liquid rises above dashed line 333, it begins to flow through channels 329 and is evenly distributed across chamber 321 between walls 324 and 325. Support means 336 elevates one end of the vaporizer so that it is oriented at an angle α with respect to horizontal, and the liquid flows toward end wall 327. A film 338 is formed, the maximum thickness t of which depends upon parameters such as surface tension, density, viscosity and the angle α. Unlike those vaporizers which confine the film within a gap between two parallel surfaces, film 338 is such that the vapor and liquid phases of the reactant are separated by a surface that is parallel to or nearly parallel to the bottom surface 323. Film thickness t must be sufficiently thin that bubbles cannot form within liquid film 338.

A second embodiment of the first stage also involves use of a vaporizer. Here, the vaporizer is a heated, vertically-extending expansion chamber which achieves vaporization when reactant is sprayed onto heated interior walls of the vaporizer. This procedure is described in U.S. patent application Ser. No. 08/368,318 to Williams, filed Dec. 30, 1994, and entitled "VERTICAL VAPORIZER FOR HALIDE-FREE SILICON CONTAINING COMPOUNDS" which is hereby incorporated by reference, and is shown in FIG. 4.

Figure 4:
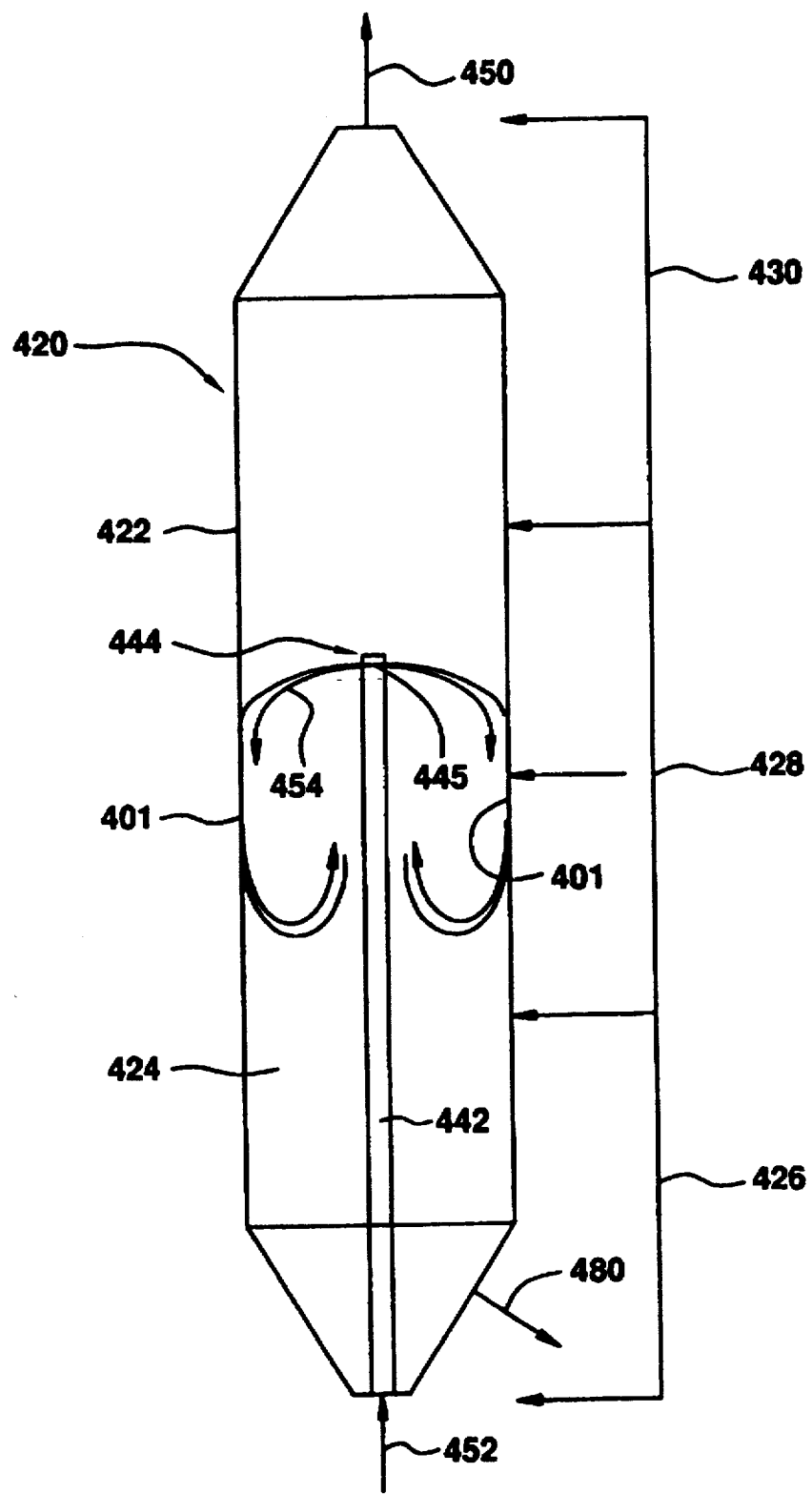
FIG. 4 is a schematic view of a second vaporizer embodiment useful in the production of optical waveguides.

As shown in FIG. 4, preheated liquid reactant is delivered to expansion chamber 420 by conduit 452 and vertical hollow shaft 442. Reactant is sprayed from shaft 442 onto chamber 420's heated walls at locations 401 through orifices 445. A portion of the liquid reactant vaporizes upon entering the interior of chamber 420 due to the pressure drop between the inside of the shaft and the inside of the chamber. The remainder of the liquid reaction forms spray 454 which passes through chamber interior 424 and contacts wall 422. This vaporizes the remaining liquid, and vapors are discharged through outlet 450. Chamber 420 includes gel collecting zone 426, middle vaporization zone 428, and superheating zone 430. Zone 426 has port 480 for removal of high molecular weight materials, which may be capable of forming gels.

In a third embodiment of the first stage, liquid reactant is delivered to a flash vaporization chamber. In that chamber, the liquid assumes the form of a thin film, vaporizes, and mixes with a gas selected from the group consisting of an inert gas, a combustible gas, an oxidizing gas, and mixtures thereof for delivery to an oxidation burner. This is described in U.S. Pat. No. 5,078,092 to Antos, et al., which is hereby incorporated by reference, and is described in FIG. 5.

Figure 5:
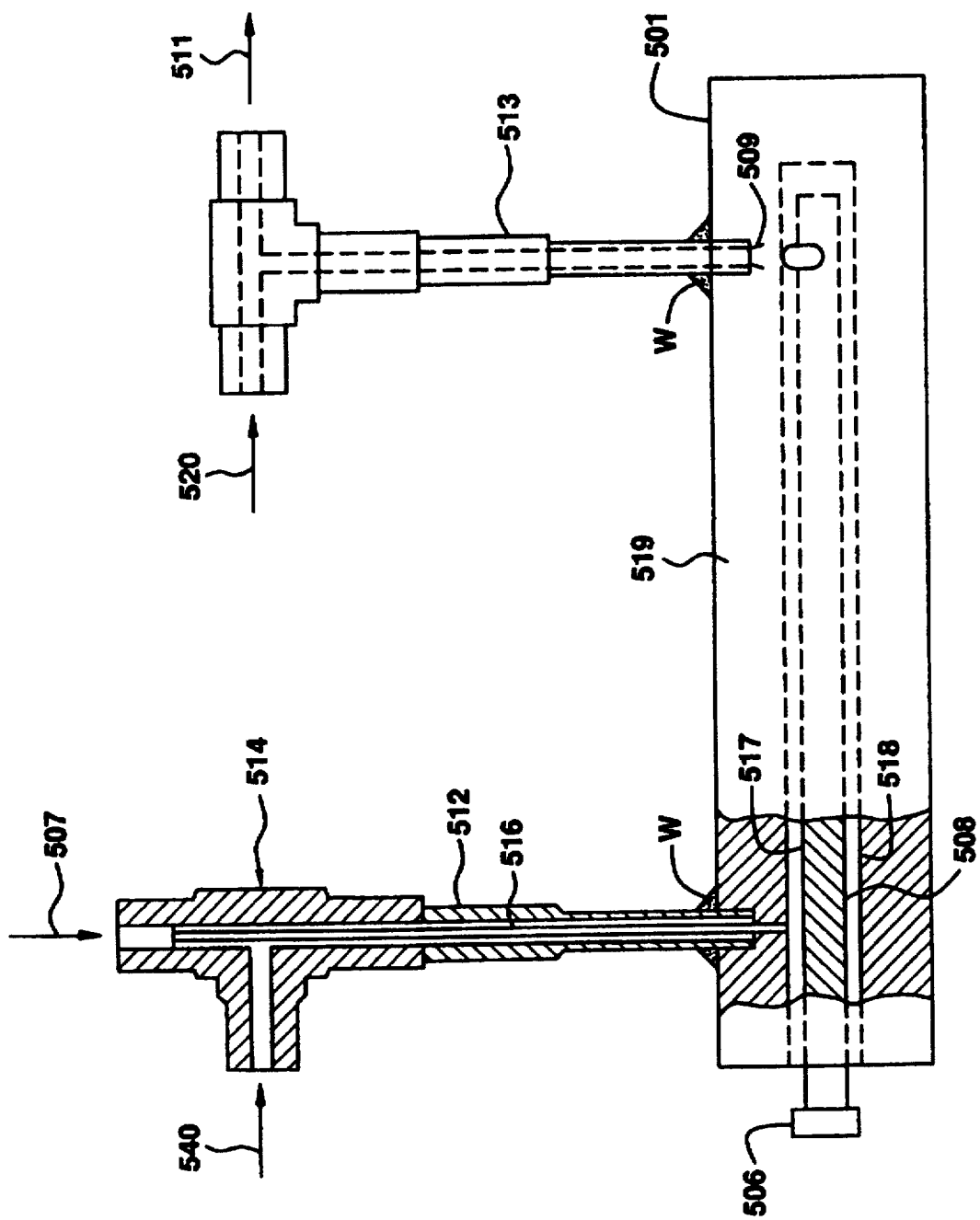
FIG. 5 is a partial cross-sectional view of a third vaporizer embodiment useful in the production of optical waveguides.

As shown in FIG. 5, liquid is delivered to flash vaporization chamber 501 by a vertical tube 516 within outer tube 512 directly onto inner surfaces 517 of heating element 506, which is formed within flash vaporization chamber 501. The liquid is fed into the top of tube 516 from feed line 507 at a controlled flow rate and is delivered to form a thin film directly onto inner surface 517, resulting in a smooth, oscillation-free vaporization. Tube 516 may comprise a 1/16th inch inner diameter vertical tube 512, connected to an 1/4th inch inner diameter Tee and tubing 514 for delivering liquid directly onto inner surface 517 as a thin film.

Flash vaporization chamber 501 is heated by heating element 506 and chamber cylinder 519. Chamber cylinder 519 may comprise several different configurations, for example a rod in cylinder or paired parallel flat plates. The temperature of heating element 506 is maintained below the temperature where nucleate or film boiling of the liquid occurs.

Figure 8:
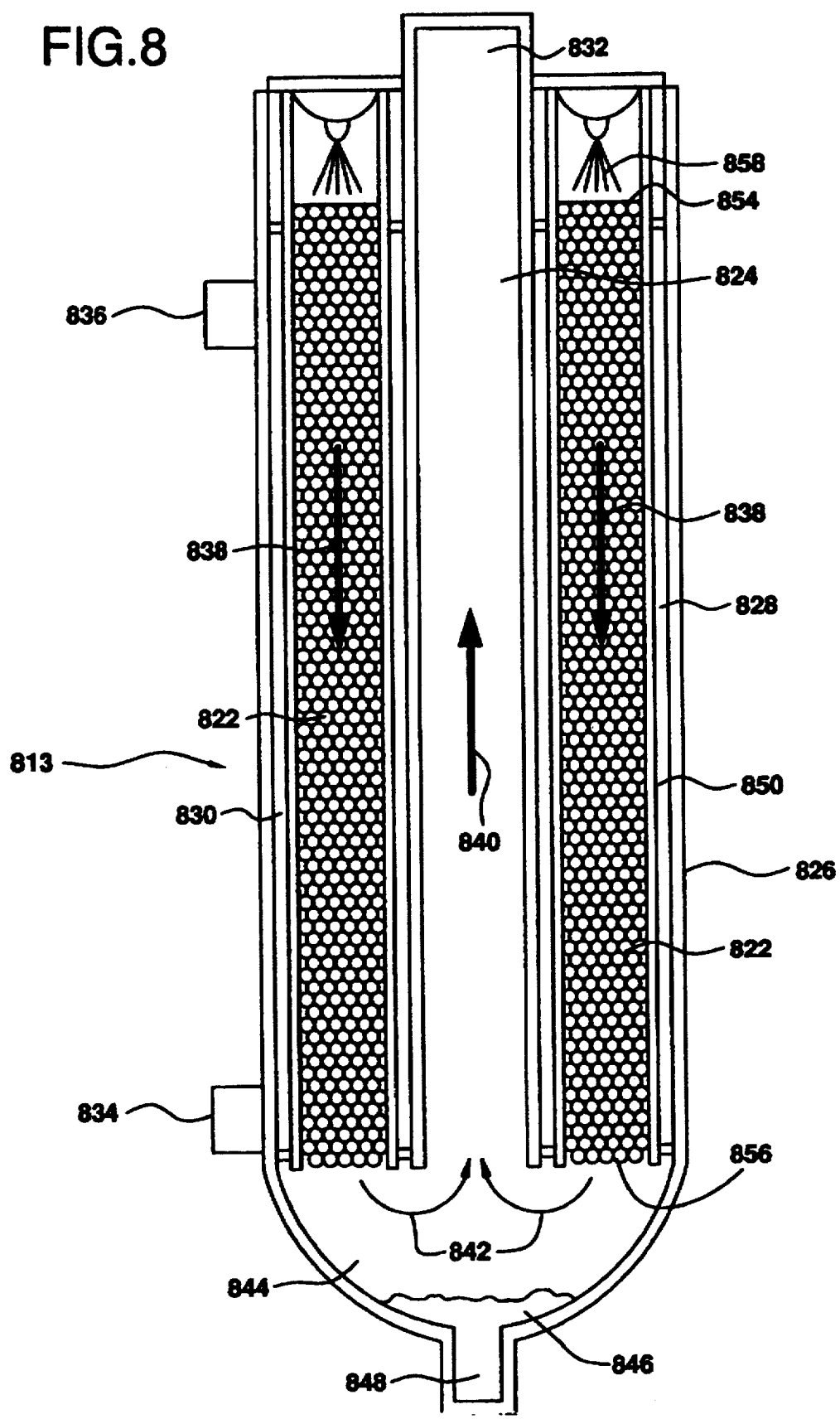
FIG. 8 is a schematic cross-sectional view of a vertical evaporator for silicon-containing compounds.

Further embodiments of vaporizers are disclosed in U.S. patent application Ser. No. 08/368,319 to Cain, filed Dec. 30, 1994 U.S. Pat. No. 5,558,687, and entitled "VERTICAL, PACKED-BED FILM EVAPORATOR FOR HALIDE-FREE, SILICON-CONTAINING COMPOUNDS," which is hereby incorporated by reference. That application discloses, as shown in FIG. 8, a vaporizer (film evaporator) 813 for halide-free, silicon-containing liquid reactants used in producing preforms. The vaporizer includes a plurality of packed-bed columns 822 surrounding central tube 824. A mixture of liquid reactant, e.g., octamethylcyclotetrasiloxane, and gas, e.g., oxygen, is sprayed onto the top surfaces 854 of the columns 822 by a set of spray nozzles 832. The liquid reactant evaporates into the gas Until the dew point temperature is reached, at which point all of the liquid reactant will have been converted into vapor. The vapor/gas mixture exits the bottom surfaces 856 of columns 822, where its direction of flow changes from downward to upward. This change in flow direction separates any high molecular weight species 846 present in the octamethylcyclotetrasiloxane from the vapor/gas mixture. The vapor/gas mixture leaves the vaporizer 813 through central tube 824 and is supplied to soot-producing burners.

Alternatively, in the first stage of optical fiber fabrication, a carrier gas is bubbled through a liquid feedstock that is maintained at a constant temperature. Optionally, each of the component liquids is separately heated to a constant temperature at which enough vapor pressure is generated to produce a reasonable rate of deposition, and the individual vapors are then combined. The resulting vaporous reactant is transported by the carrier gas, which may be an inert gas, a combustible gas, an oxidizing gas, or mixtures thereof, to a reaction site such as a burner, where the gas stream is combusted in a burner flame. In the presence of oxygen, vaporous reactants are converted to their respective oxides, exiting the burner orifice to form a gas stream containing finely-divided, amorphous, spherical particles of soot that are deposited onto a substrate, forming a porous blank or preform of opaque, white silica soot.

Figure 6A:
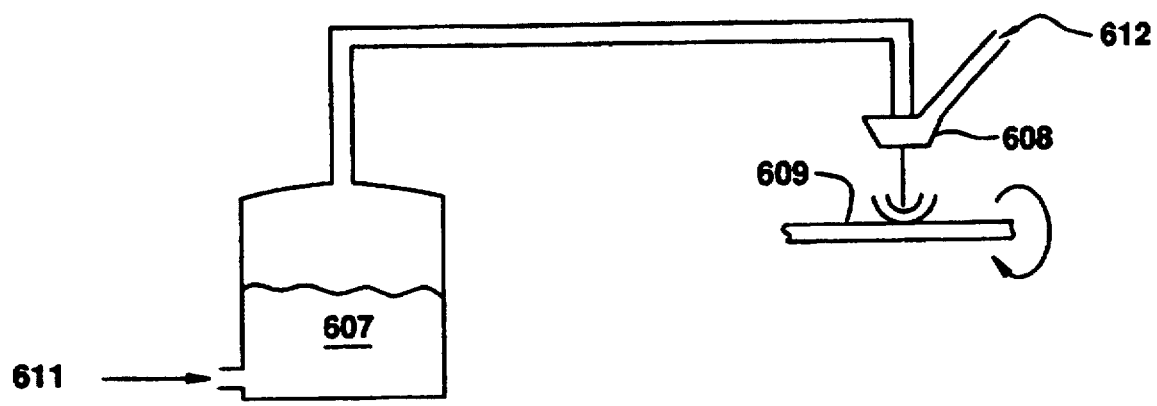
FIGS. 6A and 6B are schematic representations of an apparatus and process for depositing silica soot on a rotating mandrel to form a porous blank or preform.
Figure 6B:
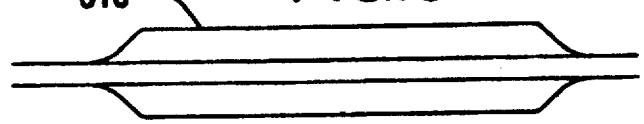
Figure 7:
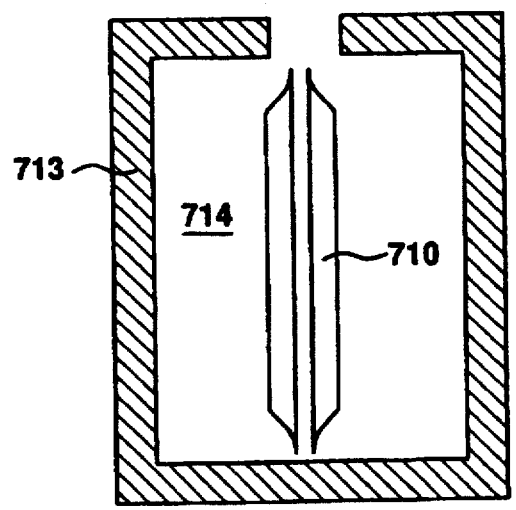
FIG. 7 is a schematic representation of a heating chamber wherein the porous blank is fired in an atmosphere of helium and chlorine to full consolidation to a non-porous body.

As depicted in FIG. 6A, feedstock 607 comprises the purified polyalkylsiloxane composition of the present invention in a standard process used in making optical waveguides. The carrier gas 611 may be, for example, a combustible gas, an oxidizing gas, an inert gas, or mixtures thereof. Nitrogen is preferably employed as the carrier gas 611 and a methane/oxygen mixture 612 is employed as the burner flame fuel, whereby combustion and oxidation are induced at the burner 608. The resulting soot is deposited on a rotating mandrel 609, thus forming a preform or blank 610 of silica soot shown at FIG. 6B. The preform is then heat treated, as shown in FIG. 7, in a consolidation furnace 713 preferably with a He/Cl$_2$ atmosphere 714 to effect full consolidation. Conventional fiber draw techniques can then be employed to make optical waveguide fiber from the consolidated preform.

Alternatively, an optical waveguide component can be formed according to the invention. In one exemplary process, soot is applied to a flat substrate to form a base cladding layer, and then further soot is deposited in two successive stages using two different reactant compositions to yield core and overcladding layers over the cladding layer on the substrate. The resultant mass is then consolidated. The design for the desired optical waveguide pathways of the component is then applied lithographically followed by etching to leave the desired waveguides superimposed on the substrate. Next, the component is overclad and the overcladding is consolidated. In a second, similar process, the final overcladding is suitably doped so that its refractive index is the same as that of the previously-deposited overcladding, but its melting point is lower so that it will easily flow in consolidation at a temperature that will not risk damaging the previously-deposited waveguides. In yet a third process, a preform is drawn into cane on which waveguides are then applied as above (see Bhagavatula U.S. Pat. No. 5,125,946 and Bhagavatula U.S. Pat. No. 5,253,319, both of which are hereby incorporated herein by reference).

In addition, the fused silica glass product of the present invention can be used to produce stepper lenses or other optical elements, e.g., conventional lenses.

EXAMPLES

The following examples further illustrate the invention.

Example 1

Atmospheric Pressure Distillation of Octamethylcyclotetrasiloxane

A five-liter flask provided with a heating mantle, distillation head, condenser, receiver flask, nitrogen purge line, and two thermometers for measuring pot and head temperatures was charged with 4000 ml of octamethylcyclotetrasiloxane (D-244), commercially available from Dow Corning, and containing 110 ppm of impurities having molecular weights greater than 520 grams per mole. The concentration of such high boiling impurities was determined by the previously described rotary evaporation procedure.

The distillation was carried out at atmospheric pressure (at about 350 meters above sea level) using a nitrogen purge to exclude oxygen, and the following fractions were collected:

| Fraction | Pot temperature (°C.) | Head temperature (°C.) | Volume (ml) |
|---|---|---|---|
| forerun | to 173 | to 166 | 500 |
| 1 | 173 | 166–167 | 850 |
| 2 | 173–174 | 167–167.5 | 850 |
| 3 | 174 | 167.5 | 850 |
| 4 | 174–175 | 167.5–171 | 750 |
| afterrun | to 189 | to 174 | 60 |

Analysis of distillation fractions 1 to 4 showed concentrations of high boiling impurities in the following concentrations:

| Fraction | ppm High Molecular Weight Impurities |
|---|---|
| 1 | 0.2 |
| 2 | 0.2 |
| 3 | 0.1 |
| 4 | 2.1 |

Thus, distillation at atmospheric pressure produced a purified polyalkylsiloxane composition (i.e. fractions 1–4) with a greatly reduced level of high boiling impurities compared to the starting material.

Example 2

Atmospheric pressure Distillation of Octamethylcyclotetrasiloxane

An atmospheric pressure (at about 350 meters above sea level) distillation of about 2.5 liters of Dow Corning D-244 octamethylcyclotetrasiloxane was carried out using substantially the same distillation apparatus as that described in Example 1.

The following distillation fractions were obtained:

| Fraction | Pot temperature (°C.) | Head temperature (°C.) | Volume (ml) |
|---|---|---|---|
| 1 | 174 | 144–162 | 30 |
| 2 | 174 | 162–167 | 270 |
| 3 | 175–176 | 168–170 | 990 |
| 4 | 176 | 170 | 15 |
| 5 | 177–179 | 170.7–172.7 | 780 |
| 6 | 180–187 | 170.5–166 | 160 |
| 7 | 190 | 162 | 60 |
| 8 | 192 | 158.5 | 15 |
| 9 | 195 | 152 | 8 |
| 10 | 199 | 146 | 6 |
| 11 | 204–210 | 140–134 | 10 |

Fraction 3, which had been collected at a rate of about 15.5 ml/min, was divided into two portions, which were concentrated under reduced pressure, using a one-liter flask connected to a rotary evaporator, to a total volume of about 5 ml. This residue was transferred to a 50-ml flask using two toluene rinses. The toluene solution was reconcentrated on the rotary evaporator to an oil. Gel permeation chromatographic analysis of this oil by the previously described procedure showed no detectable amount of high boiling material present. Thus, atmospheric pressure distillation of octamethylcyclotetrasiloxane was effective in removing the high boiling impurities that had been present.

Example 3
Improved production of Silica Glass Blanks from purified Octamethylcyclotetrasiloxane Having Low Concentrations of High Boiling Impurities Silica glass blanks were produced from several octamethylcyclotetrasiloxane feedstocks containing various concentrations of high boiling impurities. For each of the feedstocks, rate and pressure changes per blank were measured.

In addition, the number of blanks that could be produced before brushing of the burners was required was determined. Also noted was the appearance of the burner fume tubes following combustion of the feedstocks.

Shown below are the results of these tests:

| Feedstock | High Boiling Impurities (ppm) | Rate change/blank (Km/hr) | Pressure change/blank (mm Hg) | No. blanks between brushings |
|---|---|---|---|---|
| 1 | 199 | — | — | 2 |
| 2 | 161 | −4.2 | 0.82 | 4 |
| 3 | 109 | −2.2 | 0.59 | 8 |
| 4 | 17 | −1.8 | 0.37 | 10 |
| 5 | 7 | −1.9 | 0.31 | 15 |
| 6 | 4 | 0 | 0.08 | — |
| 7 | 0.6 | −0.9 | 0.11 | 22 |

The data listed above show the substantial improvements in rate and pressure changes per blank as the concentration of high boiling impurities in the feedstock was lowered from 199 to 161, then to 109, 17, 7, 4, and 0.6 ppm. Also of note is the greatly diminished burner maintenance required as the concentration of high-boiling impurities was reduced. For example, with feedstock 1, which contained 199 ppm of high boiling impurities, only two blanks could be produced before brushing of the burners was required. With feedstock 4, whose high boiling impurities concentration was 17 ppm, ten blanks were made before it was necessary to brush the burners. Use of feedstock 7, with a high boiling impurities concentration of only 0.6 ppm, enabled 22 blanks to be produced before burner maintenance was required. Feedstocks 1–3 contained about 0.05–0.2 weight percent of low boiling hexamethylcyclotrisiloxane and silanols; Feedstock 4 contained about 0.11 wt %; Feedstock 5 contained about 0.27 wt %; Feedstock 6 contained less than about 0.01 wt %; and Feedstock 7 contained about 0.19 wt %. Thus, the method of the present invention provides a surprisingly large improvement in the efficiency of fused silica glass production from purified polyalkylsiloxane feedstocks.

Inspection of the burner fume tubes after combustion of the various feedstocks showed that with feedstock 4 a moderate build-up of gel was observed on all the fume tubes. With feedstocks 5 and 7, only a small amount of gel was deposited, and not on all the fume tubes. No gel was detectable when feedstock 6 was employed in glass blank production.

The invention has been described in detail for the purpose of illustration, but it is understood that such detail is solely for that purpose, and variations can be made therein by those skilled in the art without departing from the spirit and scope of the invention, which is defined by the following claims.

What is claimed:

1. A method of purifying polyalkylsiloxanes comprising:
   providing a polyalkylsiloxane starting material containing impurities having boiling points, under atmospheric conditions, of greater than 250° C., in a total concentration of at least 14 ppm; and
   distilling the polyalkylsiloxane starting material under conditions effective to produce a purified polyalkylsiloxane composition, having a boiling point, under atmospheric conditions, of less than 250° C., and a total concentration of less than 14 ppm of said impurities having boiling points, under atmospheric conditions, of greater than about 250° C.

2. A method according to claim 1, wherein the total concentration of impurities having boiling points, under atmospheric conditions, of greater that 250° C. contained in the polyalkylsiloxane starting material is up to about 200 ppm.

3. A method according to claim 1, wherein the purified polyalkylsiloxane composition has a total concentration of less than about 6 ppm of said impurities having boiling points, under atmospheric conditions, of greater than about 250° C.

4. A method according to claim 3, wherein the purified polyalkylsiloxane composition has a total concentration of less than about 2 ppm of said impurities having boiling points, under atmospheric conditions, of greater than about 250° C.

5. A method according to claim 1, wherein the polyalkylsiloxane starting material contains impurities having molecular weights of less than about 250 grams/mole silanols; and said concentration of low boiling impurities is reduced during said and said method further comprises removing the impurities having molecular weights of less than about 250 grams/mole.

6. A method according to claim 5, wherein the impurities having molecular weights of less than about 250 grams/mole comprise hexamethylcyclotrisiloxane.

7. A method according to claim 1, wherein the purified polyalkylsiloxane composition comprises hexamethyldisiloxane.

8. A method according to claim 1 wherein the purified polyalkylsiloxane composition comprises a polymethylcyclosiloxane selected from the group consisting of hexamethylcyclotrisiloxane, octamethylcyclotetrasiloxane, decamethylcyclopentasiloxane, dodecamethylcyclohexasiloxane, and mixtures thereof.

9. A method according to claim 8, wherein the polymethylcyclosiloxane composition comprises octamethylcyclotetrasiloxane.

10. A method according to claim 1, wherein the polymethylcyclosiloxane comprises a polymethylhydrocyclosiloxane.

11. A method according to claim 9, wherein the impurities having boiling points, under atmospheric conditions, of greater than about 250° C. include a bimodal distribution of components having a median molecular weight of greater than about 900 grams per mole.

12. A method according to claim 1, wherein said providing a polyalkylsiloxane starting material comprises:
   distilling a mixture containing polyalkylsiloxanes and silanols to separate most of the silanols from the mixture to form a polyalkylsiloxane distillate; and
   passing the polyalkylsiloxane distillate through a carbon filter and a molecular sieve bed,
   thereby producing said polyalkylsiloxane starting material.

13. A polyalkylsiloxane composition produced by the method of claim 1.

14. A polyalkylsiloxane composition produced by the method of claim 3.

15. A polyalkylsiloxane composition produced by the method of claim 4.

16. A purified polyalkylsiloxane composition having a boiling point, under atmospheric conditions, of less than 250° C., and containing impurities having boiling points, under atmospheric conditions, of greater than 250° C. in a total concentration of less than 14 ppm.

17. A purified polyalkylsiloxane composition according to claim 16, wherein the purified polyalkylsiloxane composition has a total concentration of less than 6 ppm of said impurities having boiling points, under atmospheric conditions, of greater than 250° C.

18. A purified polyalkylsiloxane composition according to claim 17, wherein the purified polyalkylsiloxane composition has a total concentration of less than about 2 ppm of said impurities having boiling points, under atmospheric conditions, of greater than 250° C.

19. A purified polyalkylsiloxane composition according to claim 16, wherein the purified polyalkylsiloxane composition has a concentration of less than 14 ppm of silanol-terminated siloxanes.

20. A purified polyalkylsiloxane composition according to claim 16, wherein said composition comprises no more than about 100 ppm hexamethylcyclotrisiloxane and silanols having a molecular weight less than about 250 grams/mole.

21. A purified polyalkylsiloxane composition according to claim 16, wherein the purified polyalkylsiloxane composition comprises hexamethyldisiloxane.

22. A purified polyalkylsiloxane composition according to claim 16, wherein the purified polyalkylsiloxane composition comprises a polymethylcyclosiloxane selected from the group consisting of hexamethylcyclotrisiloxane, octamethylcyclotetrasiloxane, decamethylcyclopentasiloxane, dodecamethylcyclohexasiloxane, and mixtures thereof.

23. A purified polyalkylsiloxane composition according to claim 22, wherein the polymethylcyclosiloxane comprises octamethylcyclotetrasiloxane.

24. A purified polyalkylsiloxane composition according to claim 16, wherein the purified polyalkylsiloxane composition comprises a polymethylhydrocyclosiloxane.

25. A purified polyalkylsiloxane composition according to claim 16, wherein the impurities having boiling points, under atmospheric conditions, of greater than 250° C. include a bimodal distribution of components having a median molecular weight of greater that about 900 grams/mole.

26. A method of purifying polyalkylsiloxanes comprising:
distilling a mixture containing polyalkylsiloxanes and silanols to separate most of the silanols from the mixture to form a polyalkylsiloxane distillate;
passing the polyalkylsiloxane distillate through a carbon filter and a molecular sieve bed to produce a polyalkylsiloxane intermediate material; and
distilling the polyalkylsiloxane intermediate material under conditions effective to produce a purified polyalkylsiloxane composition and to reduce the total concentration therein of impurities having a boiling point, under atmospheric conditions, of greater than 250° C.

27. A method according to claim 26, wherein impurities having molecular weights of less than about 250 grams/mole are removed from the polyalkylsiloxane intermediate material during said distilling of the polyalkylsiloxane intermediate material.

28. A method according to claim 27, wherein the impurities having molecular weights of less than about 250 grams/mole comprise hexamethylcyclotrisiloxane.

29. A method according to claim 26, wherein the purified polyalkylsiloxane composition comprises hexamethyldisiloxane.

30. A method according to claim 26, wherein the purified polyalkylsiloxane composition comprises a polymethylcyclosiloxane selected from the group consisting of hexamethylcyclotrisiloxane, octamethylcyclotetrasiloxane, decamethylcyclopentasiloxane, dodecamethylcyclohexasiloxane, and mixtures thereof.

31. A method according to claim 30, wherein the polymethylcyclosiloxane comprises octamethylcyclotetrasiloxane.

32. A method according to claim 26, wherein the purified polyalkylsiloxane composition comprises a polymethythydrocyclosiloxane.

33. A polyalkylsiloxane composition produced by the method of claim 26.

* * * * *

UNITED STATES PATENT AND TRADEMARK OFFICE
CERTIFICATE OF CORRECTION

PATENT NO. : 5,703,191
DATED : December 30, 1997
INVENTOR(S) : Danny L. Henderson, et al.

It is certified that error appears in the above-identified patent and that said Letters Patent is hereby corrected as shown below:

Column 16, lines 25-27: delete -- silanols; and said concentration of low boiling impurities is reduced during said --

Signed and Sealed this

Twenty-seventh Day of July, 1999

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,703,191
DATED : December 30, 1997
INVENTOR(S) : Danny L. Henderson and Dale R. Powers It is certified that error appears in the above-identified patent and that said Letters Patent is hereby corrected as shown below:

<u>Title page,</u>
Item [63], Related U.S. Application Data, the following wording should appear
-- This application claims the benefit of and priority to Application US Serial Number 60/003,116, filed September 1, 1995 --.

<u>Column 1,</u>
Line 12, the following wording should appear -- This application claims the benefit of and priority to Application US Serial Number 60/003,116, filed September 1, 1995 --.

Signed and Sealed this

Seventeenth Day of December, 2002

JAMES E. ROGAN
*Director of the United States Patent and Trademark Office*